United States Patent
Suzuki et al.

(10) Patent No.: US 8,623,405 B2
(45) Date of Patent: Jan. 7, 2014

(54) FINELY DIVIDED COMPOSITION CONTAINING POORLY WATER SOLUBLE SUBSTANCE

(75) Inventors: Hiroshi Suzuki, Osaka (JP); Tomohiro Yoshinari, Osaka (JP); Naomi Nagaoka, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 1001 days.

(21) Appl. No.: 11/795,734

(22) PCT Filed: Jan. 27, 2006

(86) PCT No.: PCT/JP2006/301816
§ 371 (c)(1),
(2), (4) Date: Dec. 6, 2007

(87) PCT Pub. No.: WO2006/087919
PCT Pub. Date: Aug. 24, 2006

(65) Prior Publication Data
US 2008/0118552 A1 May 22, 2008

(30) Foreign Application Priority Data
Jan. 28, 2005 (JP) .................. 2005-022124

(51) Int. Cl.
*A61K 9/48* (2006.01)
*A61K 9/20* (2006.01)
*A61K 47/30* (2006.01)
*A61K 9/28* (2006.01)
*A61K 9/14* (2006.01)

(52) U.S. Cl.
USPC ........... 424/451; 424/464; 424/474; 424/489; 424/497; 514/772.3

(58) Field of Classification Search
None
See application file for complete search history.

(56) References Cited

U.S. PATENT DOCUMENTS

| | | | |
|---|---|---|---|
| 5,145,684 A | * | 9/1992 | Liversidge et al. ........... 424/489 |
| 5,534,270 A | | 7/1996 | DeCastro |
| 5,552,160 A | * | 9/1996 | Liversidge et al. ........... 424/489 |
| 2002/0068641 A1 | | 6/2002 | Dicicco |
| 2002/0119200 A1 | | 8/2002 | Haskell |
| 2003/0068280 A1 | | 4/2003 | Bannister et al. |
| 2004/0037785 A1 | | 2/2004 | Staniforth et al. |
| 2004/0053972 A1 | | 3/2004 | Nara |
| 2005/0023386 A1 | | 2/2005 | Haskell |
| 2005/0090530 A1 | | 4/2005 | Leonard et al. |

FOREIGN PATENT DOCUMENTS

| | | | |
|---|---|---|---|
| JP | 9-206000 | | 8/1997 |
| JP | 11-79985 | | 3/1999 |
| JP | 2004-99442 | | 4/2004 |
| WO | WO 03/045945 | * | 6/2003 ........... C07D 417/12 |

OTHER PUBLICATIONS

Jacobs et al, 2000. Nanosuspensions as a new approach for the formulation for the poorly soluble drug tarazepide. International Journal of Pharmaceutics, vol. 196:161-164.*
International Search Report for International Publication: PCT/JP2006/301816 dated May 16, 2006.

* cited by examiner

*Primary Examiner* — Shanon A Foley
(74) *Attorney, Agent, or Firm* — Hamre, Schumann, Mueller & Larson, P.C.

(57) ABSTRACT

The disclosed method involves preparation of a composition containing a poorly water soluble substance. The composition has a median diameter of not more than 1 μm, and includes (i) a poorly water soluble substance, (ii) polyvinylpyrrolidone or a vinylpyrrolidone-vinyl acetate copolymer, and (iii) an auxiliary dispersion stabilizer. By employing such constitution, a poorly water soluble substance is sufficiently micronized and a composition containing a poorly water soluble substance showing good absorbability of the poorly water soluble substance can be provided.

28 Claims, 2 Drawing Sheets

FINELY DIVIDED COMPOSITION CONTAINING POORLY WATER SOLUBLE SUBSTANCE

TECHNICAL FIELD

The present invention relates to a composition comprising a poorly water soluble substance, used in the fields of drugs, foods and the like, more specifically to a composition wherein the absorbability of a poorly water soluble substance is improved, a method of producing the same, and a use thereof.

BACKGROUND ART

As techniques for improving the absorption of a poorly water soluble substance from the gastrointestinal tract and suppressing the variation thereof, solubilization by the addition of cyclodextrin and the like, solid dispersion and micronization are known (International Patent Publication Nos. WO96/019239 and WO02/048142). Hence, it is known that poorly water soluble substance is micronized to improve the absorption of a poorly water soluble substance and to suppress the variation in the absorption. However, as a method of micronizing a poorly water soluble substance, dry pulverization using jet mill and the like is commonly used; in the dry pulverization, because the surface area increases with the progress of pulverization, resulting in re-aggregation, it is difficult to micronize a poorly water soluble substance until the median diameter becomes not more than several microns (that is, the particle size reached is up to several microns as the median diameter).

On the other hand, to obtain microparticles not more than several microns, it is common practice to use a build-up method such as crystallization, wherein particles are formed from a dissolved state with gradually increasing sizes. However, in build-up methods such as crystallization, because it is usually necessary to dissolve the poorly water soluble substance once in a good solvent such as an organic solvent, and then add the solution to a poor solvent, various crystallization conditions must be carefully evaluated for each kind of poorly water soluble substance to be micronized, which involves complicated operation. Also, because a poorly water soluble substance micronized by the build-up method to the extent that makes the median diameter to be not more than several microns is microcrystalline unlike in the crystallization operation for preparing macrocrystals for purification, the solvent and the like used are likely to remain as residues. It is hard to obtain pure microparticles. Particularly, when the build-up method is used in the pharmaceutical field, there is a problem in which if a solvent other than water remains as a residue, the residual amount must be measured and safety must be assured.

Also, wet pulverization usually enables pulverization to finer particle sizes than dry pulverization, but because the pulverization performance differs depending on the choice of dispersion stabilizer and the amount added, it is necessary to carefully evaluate the pulverization formula (choice of dispersion stabilizer and the amount added) for each kind of poorly water soluble substance. Even when the pulverization formula is prepared, it is not always easy to micronize the formulation to the extent that the median diameter is not more than several microns; it has been substantially difficult to sufficiently improve the absorption of a poorly water soluble substance or suppress the variation in the absorption.

In view of the above-described situation, the present invention is intended to provide a micronized composition comprising a poorly water soluble substance wherein the poorly water soluble substance is sufficiently micronized to improve the absorbability of the poorly water soluble substance (preferably absorption is improved and variation in absorption is suppressed), and a method of producing the same, and a use thereof.

DISCLOSURE OF THE INVENTION

The present inventors diligently investigated with the aim of accomplishing the above-described objects, found that when a composition prepared by blending a poorly water soluble substance with polyvinylpyrrolidone or a vinylpyrrolidone-vinyl acetate copolymer is pulverized by wet pulverization, suitably when a composition prepared by blending a poorly water soluble substance with polyvinylpyrrolidone or a vinylpyrrolidone-vinyl acetate copolymer and further with an auxiliary dispersion stabilizer is pulverized by wet pulverization, surprisingly, the poorly water soluble substance is efficiently micronized independently of the properties of the poorly water soluble substance, and the absorbability thereof was improved, and developed the present invention.

Accordingly, the present invention provides the following:
(1) A composition having a median diameter of not more than 1 μm, comprising (i) a poorly water soluble substance and (ii) polyvinylpyrrolidone or a vinylpyrrolidone-vinyl acetate copolymer.
(2) A composition having a median diameter of not more than 1 μm, comprising (i) a poorly water soluble substance, (ii) polyvinylpyrrolidone or a vinylpyrrolidone-vinyl acetate copolymer and (iii) an auxiliary dispersion stabilizer.
(3) The composition described in (1) or (2) above, having a 90% frequency particle diameter of not more than 2 μm.
(4) The composition described in (1) or (2) above, wherein (i) the poorly water soluble substance occurs as crystalline microparticles.
(5) The composition described in (1) or (2) above, wherein the solubility of the poorly water soluble substance in water at 37° C. is not less than 1 μg/ml and not more than 0.1 mg/ml.
(6) The composition described in (2) above, wherein the auxiliary dispersion stabilizer is at least one selected from the group consisting of surfactants, hydrophilic polymers, cyclodextrin derivatives and cholic acid derivatives.
(7) The composition described in (6) above, wherein the surfactant is at least one selected from the group consisting of anionic surfactants, cationic surfactants and nonionic surfactants.
(8) The composition described in (2) above, wherein the auxiliary dispersion stabilizer is a long-chain alkyl sulfate salt.
(9) The composition described in (8) above, wherein the long-chain alkyl sulfate salt is sodium lauryl sulfate.
(10) The composition described in (8) above, wherein the solubility of the poorly water soluble substance in water at 37° C. is less than 1 μg/ml.
(11) The composition described in (1) above, wherein the content ratio by weight of (i) the poorly water soluble substance and (ii) the polyvinylpyrrolidone or vinylpyrrolidone-vinyl acetate copolymer is 99.99 to 85.0:0.01 to 15.0.
(12) The composition described in (2) above, wherein the content ratio by weight of (i) the poorly water soluble substance, (ii) the polyvinylpyrrolidone or vinylpyrrolidone-vinyl acetate copolymer, and (iii) the auxiliary dispersion stabilizer is 99.98 to 80.0:0.01 to 15.0:0.01 to 5.0.
(13) The composition described in (1) or (2) above, prepared as a powdery solid composition.

(14) The composition described in (1) or (2) above, used in a suspension wherein the composition is dispersed in a liquid.
(15) The composition described in (1) or (2) above, intended for oral administration.
(16) A composition having a median diameter of not more than 1 μm, prepared by pulverizing (i) a poorly water soluble substance and (ii) polyvinylpyrrolidone or a vinylpyrrolidone-vinyl acetate copolymer.
(17) A composition having a median diameter of not more than 1 μm, prepared by pulverizing (i) a poorly water soluble substance, (ii) polyvinylpyrrolidone or a vinylpyrrolidone-vinyl acetate copolymer and (iii) an auxiliary dispersion stabilizer.
(18) A method of producing the composition described in (1) above, comprising a step for pulverizing (i) a poorly water soluble substance and (ii) polyvinylpyrrolidone or a vinylpyrrolidone-vinyl acetate copolymer in a liquid.
(19) A method of producing the composition described in (2) above, comprising a step for pulverizing (i) a poorly water soluble substance, (ii) polyvinylpyrrolidone or vinylpyrrolidone-vinyl acetate copolymer and (iii) an auxiliary dispersion stabilizer in a liquid.
(20) The method described in (18) or (19) above, wherein the solid concentration of (i) the poorly water soluble substance in a liquid is 10 to 60% by weight.
(21) The method described in (18) or (19) above, wherein the liquid is water.
(22) The method described in (18) or (19) above, comprising pulverization using a high-pressure homogenizer.
(23) The method described in (22) above, wherein the pressure exerted on the high-pressure homogenizer is not less than 500 bar and not more than 5000 bar.
(24) The method described in (22) above, wherein provided that (i) the poorly water soluble substance has a melting point of not less than 140° C., the temperature of the composition just before flowing in the pulverization portion during operation of the high-pressure homogenizer is lower by not less than 100° C. than the melting point of (i) the poorly water soluble substance.
(25) The method described in (22) above, wherein provided that (i) the poorly water soluble substance has a melting point of less than 140° C., the temperature of the composition just before flowing in the pulverization portion during operation of the high-pressure homogenizer is not more than 40° C.
(26) The method described in (22) above, wherein provided that (i) the poorly water soluble substance has crystalline polymorphs, and the melting point of the crystalline polymorph having the lowest melting point is not less than 140° C., the temperature of the composition just before flowing in the pulverization portion during operation of the high-pressure homogenizer is lower by not less than 100° C. than the melting point of (i) the poorly water soluble substance.
(27) The method described in (22) above, wherein provided that (i) the poorly water soluble substance has crystalline polymorphs, and the melting point of the crystalline polymorph having the lowest melting point is less than 140° C., the temperature of the composition just before flowing in the pulverization portion during operation of the high-pressure homogenizer is not more than 40° C.
(28) A method of producing the composition described in (1) above, comprising a step for pulverizing (i) a poorly water soluble substance and (ii) polyvinylpyrrolidone or a vinylpyrrolidone-vinyl acetate copolymer in a liquid, and powdering the same.
(29) A method of producing the composition described in (2) above, comprising a step for pulverizing (i) a poorly water soluble substance, (ii) polyvinylpyrrolidone or a vinylpyrrolidone-vinyl acetate copolymer and (iii) an auxiliary dispersion stabilizer in a liquid, and powdering the same.
(30) A drug or food comprising the composition described in (1) or (2) above.
(31) The drug or food described in (30) above, prepared as a solid preparation.
(32) The drug or food described in (31) above, wherein the solid preparation is in the form of tablets.
(33) The drug or food described in (32) above, wherein the tablets are film-coated tablets.
(34) The drug or food described in (31) above, wherein the solid preparation is in the form of granules or powders.
(35) The drug or food described in (34) above, wherein the granules are film-coated granules.
(36) The drug or food described in (31) above, wherein the solid preparation is in the form of a capsular preparation.
(37) The drug or food described in (31) above, wherein the solid preparation is a sustained-release preparation.

As mentioned herein, "absorption (absorbability)" means "absorption (absorbability) from the gastrointestinal tract", and "variation in absorption" means variation in the amount absorbed due to individual differences and day-to-day change in the in vivo environment, dietary conditions and the like.

BEST MODE FOR EMBODYING THE INVENTION

Figure 1:
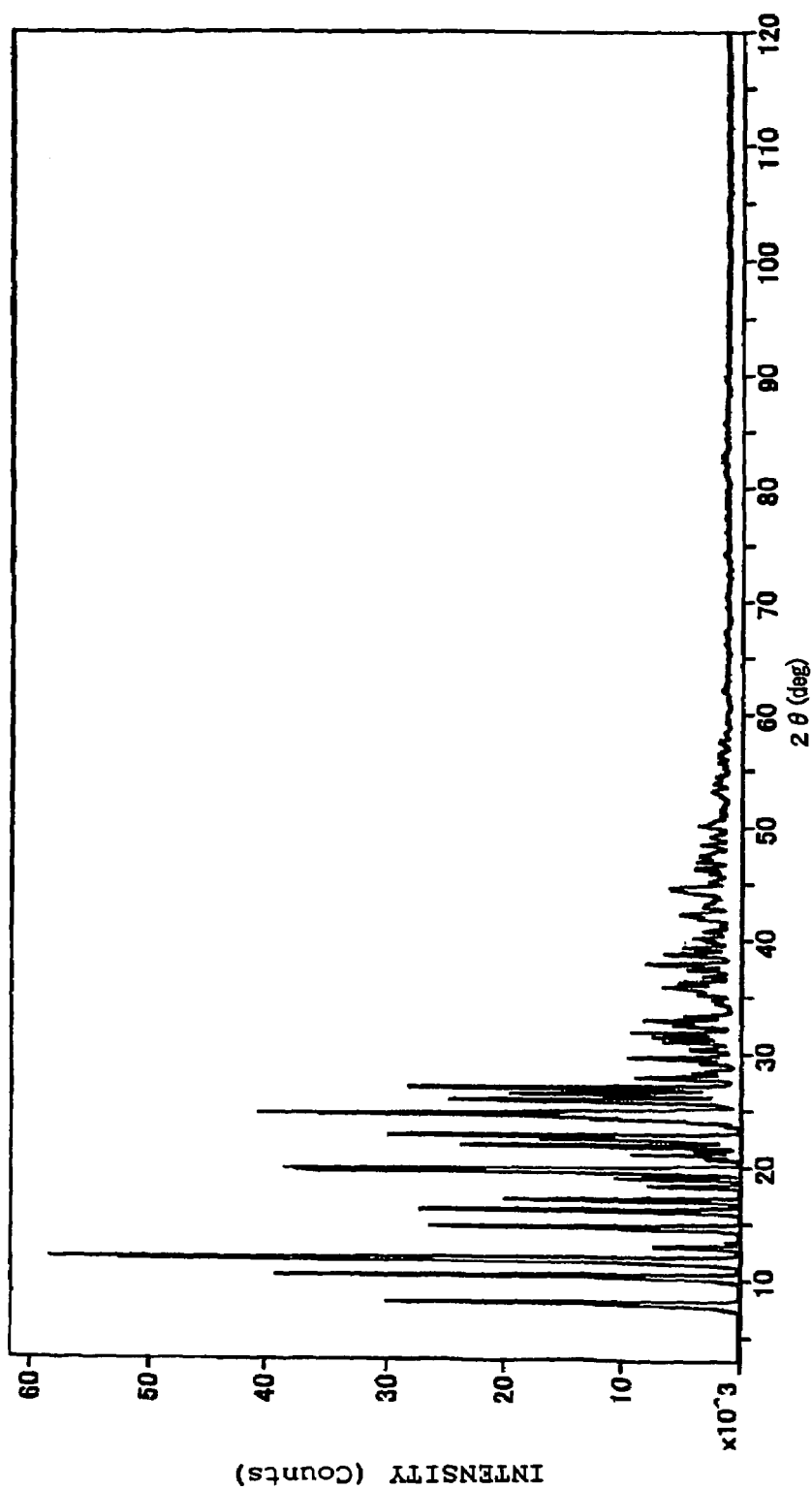
FIG. 1 is a powder X-ray diffraction chart of nifedipine (before pulverization).

The present invention is hereinafter described in more detail.

The present invention provides a composition having a median diameter of not more than 1 μm, comprising (i) a poorly water soluble substance and (ii) polyvinylpyrrolidone or a vinylpyrrolidone-vinyl acetate copolymer, preferably a composition having a median diameter of not more than 1 μm, comprising (i) a poorly water soluble substance, (ii) polyvinylpyrrolidone or a vinylpyrrolidone-vinyl acetate copolymer and (iii) an auxiliary dispersion stabilizer. "A composition having a median diameter of not more than 1 μm" means "comprising a poorly water soluble substance having a median diameter of not more than 1 μm".

The present invention is applicable to a broad range of compositions comprising a poorly water soluble substance as an active ingredient in drugs, quasi-drugs, foods and the like.

As examples of "(i) a poorly water soluble substance" used in the present invention, synthetic compounds, fermentation products, peptides, proteins, cells, tissue extracts and the like can be mentioned; the poorly water soluble substance is not subject to limitation, as long as it is one exhibiting low absorption due to low solubility or one exhibiting a variation in absorption due to individual differences and day-to-day change in the in vivo environment, dietary conditions and the like.

As mentioned herein, "individual differences in the in vivo environment" refers to, for example, differences in intragastric pH level in patients with anacidity or hypoacidity from healthy humans; "day-to-day variation in the in vivo environment" refers to, for example, differences in intragastric pH level among different days in patients with hypoacidity. "Dietary conditions" refers to differences in the timing of intake relative to mealtimes and differences in the contents of meals. "Differences in the contents of meals" is, for example, a difference in the balance or quantity of nutritive components of high-calorie diets, low-calorie diets and the like. A poorly water soluble substance has the solubility thereof differing depending on the change in these conditions of the in vivo environment, often resulting in a change in the absorption.

In the present invention, the poorly water soluble substance can be a free form or a salt. As examples of the salt, pharmacologically acceptable salts such as those with metals, those with inorganic acids, those with organic acids, and those with acidic amino acids can be mentioned. As preferable examples of metal salts, alkali metal salts such as sodium salts and potassium salts; alkaline earth metal salts such as calcium salts, magnesium salts, and barium salts; zinc salts and the like can be mentioned. As preferable examples of salts with inorganic acids, salts with hydrochloric acid, hydrobromic acid, nitric acid, sulfuric acid, phosphoric acid and the like can be mentioned. As preferable examples of salts with organic acids, salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like can be mentioned. As preferable examples of salts with acidic amino acids, salts with aspartic acid, glutamic acid and the like can be mentioned.

The poorly water soluble substance used in the present invention can be of low biological membrane permeability, as long as it is nutritionally or pharmacologically useful. The poorly water soluble substance can be a prodrug thereof. With respect to molecular weight, there is no particular limitation. As used herein, "biological membrane permeability" refers to the apparent membrane permeability of the substance in the gastrointestinal tract mucosa involved in the absorption of the substance.

When the composition of the present invention is for pharmaceutical use, examples of the poorly water soluble substance include drugs such as antibacterial drugs, antifungal drugs, osteoporosis remedies, antitumor drugs, anticancer drugs, infectious disease remedies, antidepressants, anti-HIV drugs, immunosuppressants, pharmaceutical agents affecting the central nervous system, hypnotic analgesics, anti-anxiety drugs, anti-epileptic drugs, antipyretic analgesic anti-inflammatory agents, analeptics, stimulants, antiperkinson drugs, skeletal muscle relaxants, autonomics, antispasmodics, cardiotonics, antiarrhythmic agents, antihypertensives (hypotensors), vasodilators, antihyperlipemic agents, cardiovascular drugs, respiratory stimulants, antitussives, expectorants, bronchodilators, and antidiabetic drugs.

When the composition of the present invention is for food use, examples of the poorly water soluble substance include vitamins such as vitamin A, vitamin B2, vitamin D, vitamin E, vitamin K and vitamin P, vitamin-like substances such as α-lipoic acid and coenzyme Q10, minerals such as calcium salts and heme iron and the like.

The present invention is applicable to poorly water soluble substance having a solubility in water of, for example, not more than 0.1 mg/ml at 37° C., and further to poorly water soluble substance having a solubility of not more than 0.05 mg/ml at 37° C.; preferably, the lower limit of the solubility of the poorly water soluble substance in water is not less than 1 μg/ml at 37° C. However, in the mode wherein the composition of the present invention comprises (i) a poorly water soluble substance, (ii) polyvinylpyrrolidone or a vinylpyrrolidone-vinyl acetate copolymer and (iii) an auxiliary dispersion stabilizer, and (iii) the auxiliary dispersion stabilizer is an anionic surfactant (preferably a long-chain alkyl sulfate salt such as sodium lauryl sulfate), a sufficient absorption-improving effect can be obtained even on a poorly water soluble substance having a solubility in water of less than 1 μg/ml at 37° C.

The term solubility as mentioned herein refers to the amount of poorly water soluble substance in the filtrate obtained by adding the poorly water soluble substance in excess to purified water (manufactured by Millipore, Milli-Q System (trade name)), allowing the mixture to stand in a constant-temperature chamber at 37° C. for 2 hours, during which period samples were taken every 30 minutes, stirring each sample in a volutex mixer, and filtering the resulting suspension through a syringe filter (manufactured by Nihon Pall Ltd., Acrodisc LC25, PVDF, pore diameter 0.2 μm).

Although the poorly water soluble substance used in the present invention can be crystalline or amorphous, it is preferably crystalline. Hence, when the poorly water soluble substance is crystalline, the chemical stability and physical stability of the poorly water soluble substance are improved. Whether the poorly water soluble substance is crystalline or amorphous can be determined by the presence or absence of a diffraction peak in powder X-ray crystal diffraction. In the present invention, poorly water soluble substances can be used singly or in combination of two or more kinds.

Although the molecular weight of the "(ii) polyvinylpyrrolidone (hereinafter also abbreviated "PVP") or a vinylpyrrolidone-vinyl acetate copolymer (hereinafter also abbreviated "PVP-PVAc")" used in the present invention is not subject to limitation, one having a relatively low molecular weight is preferable, and the relative viscosity (25° C.) is preferably not more than 5.195, more preferably not more than 1.281, and particularly preferably not more than 1.201. In the case of one having a higher relative viscosity (25° C.), it can be used with the amount added thereof reduced. The PVP-PVAc can be a random copolymer or a block copolymer, and the copolymerization ratio of vinylpyrrolidone and vinyl acetate (vinylpyrrolidone:vinyl acetate) is not subject to limitation, but is preferably 99.99:0.01 to 2:8 (molar ratio), more preferably 99.99:0.01 to 5:5 (molar ratio).

Specifically, as examples of PVP, "Kollidon 90F" (trade name), manufactured by BASF Takeda Vitamin K.K., (relative viscosity (25° C.): 3.310 to 5.195), "Kollidon 30" (trade name) (relative viscosity (25° C.): 1.201 to 1.281), "Kollidon 25" (trade name) (relative viscosity (25° C.): 1.146 to 1.201) "Kollidon 17PF" (trade name) (relative viscosity (25° C.): 1.430 to 1.596) "Kollidon 12PF" (trade name) (relative viscosity (25° C.): 1.222 to 1.361) and the like can be mentioned. As examples of PVP-PVAc, "Copovidone VA64" (trade name), manufactured by BASF Takeda Vitamin K.K., (relative viscosity (25° C.): 1.178 to 1.255) can be mentioned.

"Relative viscosity (25° C.)" as used herein is a value measured at a concentration of 1% (wt./vol) at 25° C. using purified water as the solvent by the method described in USP and Ph. Eur. Monograph. However, the above-described relative viscosities (25° C.) of "Kollidon 17PF" and "Kollidon 12PF" are measurements at a concentration of 5% (wt./vol).

(iii) The auxiliary dispersion stabilizer used in the present invention can be used without limitation, as long as it is capable of improving the dispersion stability of a poorly water soluble substance. For example, nonionic surfactants (for example, polyoxyethylene alkyl ethers, polyethylene glycol fatty acid esters, polyoxypropylene alkyl ethers, polypropylene glycol fatty acid esters, sorbitan fatty acid esters, polyoxyethylene sorbitan fatty acid esters, polyoxyethylene hardened castor oil, polyglycerin fatty acid esters, polyoxyethylene glycerin fatty acid esters, glycerin monofatty acid esters, alkyl polyglucoside, polyoxyethylene polyoxypropylene block polymers, alkanolamide and the like), ampholytic surfactants (betaine alkyldimethylaminoacetate, betaine amidopropyldimethylaminoacetate, amide aminoacid salts, alkyliminodiacetate and the like), anionic surfactants (for example, alkyl sulfate, alkyl ether sulfate, α-olefin sulfonate, acylmethyltaurate, acylglutamate, acylglycine salt, acylsarcosine salt, acylisethionate, alkyl ethercarboxylate, amide ether sulfate, alkylphosphate ester salt and the like), cationic surfactants (for example, alkyltrimethylammonium chloride, dialkyldimethylammonium chloride and the like), bile acid and salts thereof, soaps and fatty acids, and salts thereof, oils, glycerin fatty acid esters, enamine, chelating agents, phenothiazine, carnitine or peptide fatty acid derivatives, a substance selected from the group consisting of azone, concanavalin A, diethyl maleate and diethylethoxymethylene malonate, Maillard reaction products, and polymers (for example, block copolymers and biodegradable polymers, chitosan and chitosan derivatives) can be mentioned. Of these, surfactants, hydrophilic polymers, cyclodextrin derivatives, cholic acid derivatives and the like are preferable, and surfactants are particularly preferable. Of the surfactants, at least one selected from among anionic surfactants, cationic surfactants and nonionic surfactants is preferable, particularly preferably an anionic surfactant; of anionic surfactants, long-chain alkyl (preferably having a carbon number of 10 to 20) sulfate are preferable, and sodium lauryl sulfate is most preferable. The sodium lauryl sulfate mentioned herein is a single substance. In the present invention, auxiliary dispersion stabilizer can be used singly or in combination of two or more kinds.

The composition of the present invention comprises at least (i) poorly water soluble substance and (ii) PVP or PVP-pvaC, wherein provided that (iii) an auxiliary dispersion stabilizer is not contained, the content ratio by weight of (i) poorly water soluble substance and (ii) PVP or PVP-PVAc [(i) poorly water soluble substance: (ii) PVP or PVP-PVAc] is preferably 99.99 to 85.0:0.01 to 15.0, more preferably 99.95 to 85.0:0.05 to 15.0.

When the composition of the present invention is a composition further comprising (iii) an auxiliary dispersion stabilizer, along with (i) poorly water soluble substance and (ii) PVP or PVP-PVAc, the content ratio by weight of (i) the poorly water soluble substance, (ii) the PVP or PVP-PVAc, and (iii) the auxiliary dispersion stabilizer [(i) poorly water soluble substance: (ii) PVP or PVP-PVAc: (iii) auxiliary dispersion stabilizer] is preferably 99.98 to 80.0:0.01 to 15.0: 0.01 to 5.0, more preferably 99.98 to 82.0:0.01 to 15.0:0.01 to 3.0.

The composition of the present invention is prepared by taking a step for pulverizing (i) a poorly water soluble substance and (ii) PVP or PVP-PVAc in a liquid (hereinafter also referred to as "wet pulverization"), or by pulverizing (i) a poorly water soluble substance (ii) PVP or PVP-PVAc, and (iii) an auxiliary dispersion stabilizer in a liquid (step A). In the step A, the solid concentration of the poorly water soluble substance in the liquid is preferably 10 to 60% (wt/wt), more preferably 20 to 60% (wt/wt), most preferably 20 to 40% (wt/wt). Here, the solid concentration of the poorly water soluble substance is calculated by dividing the weight of the poorly water soluble substance contained in the suspension by the weight of the liquid.

In the present invention, although the liquid used for the above-described wet pulverization is preferably water, organic solvents, oils, and heat-melted organic liquids (for example, molten liquid of wax and the like) can also be used, and the liquid can be a mixture prepared by mixing these organic liquids in water. Milling operation can be performed using a commonly known method of wet pulverization; for example, the method using a grinding container and pulverization ball, described in "Chemical Pharmaceutical Bulletin, Vol. 41, pp. 737 to 740, 1993", the method using a high-pressure homogenizer, described in "International Journal of Pharmaceutics, Vol. 196, pp. 161 to 164, 2000", a method using a media mill (for example, a method using a rod mill, a method using a roller mill and the like) and the like. The above-described method using a grinding container and pulverization ball is a method using what is called a method using a ball mill, classified as a method using a media mill. In the methods using a media mill, such as the method using a ball mill, impurity contamination of the composition obtained is of concern, whereas the high-pressure homogenizer produces extremely low levels of impurity contamination of the composition. Therefore, in case of drugs and foods, because impurity contamination of the composition obtained is unwanted, it is preferable, from the viewpoint of impurity contamination of the composition, to perform pulverization using a high-pressure homogenizer.

In wet pulverization in the present invention, when a poorly water soluble substance having a low chemical stability is used, the chemical stabilizer can be added to pulverization formula. As examples of the chemical stabilizer, antioxidants such as citric acid, vitamin C, vitamin E, vitamin C sodium, erythorbic acid, and dibutylhydroxy toluene can be mentioned. If the chemical stability of the poorly water soluble substance can be improved by changing the pH of the liquid, pH regulators such as citric acid and sodium citrate can be mentioned. The amount of chemical stabilizer added is not subject to limitation, but when the composition is a drug, it is preferable that the amount of additive added per day should not exceed levels that have been used in actual clinical settings. If the levels are exceeded, safety must be confirmed. When a substance for use as is in clinical treatment, for example, vitamin C, is added for any purpose other than treatment, it is stated in the "Guidelines for Manufacture of Drugs 2001" (published by Jiho, Inc.) that the amount added is set at a level not more than 1/5 of the minimum clinical dose, and this rule is followed in the present invention as well.

Milling using a high-pressure homogenizer is preferably performed under conditions involving a pressure of not less than 500 bar and not more than 5000 bar exerted on the high-pressure homogenizer, more preferably under conditions involving a pressure of not less than 1000 bar and not more than 3000 bar exerted on the high-pressure homogenizer.

When (i) poorly water soluble substance has a melting point of not less than 140° C., it is preferable that the temperature of the composition just before flowing in the pulverization portion during operation of the high-pressure homogenizer be a temperature lower by not less than 100° C. (preferably a temperature lower by not less than 110° C.) than the melting point of (i) poorly water soluble substance. By doing so, the elasticity of the poorly water soluble substance can sometimes be nullified, a feature suitable for pulverization.

When (i) poorly water soluble substance has a melting point of less than 140° C., it is preferable that the temperature of the composition just before flowing in the pulverization portion during operation of the high-pressure homogenizer be not more than 40° C. (preferably not more than 30° C.). By doing so, the elasticity of the poorly water soluble substance can sometimes be nullified, a feature suitable for pulverization.

The compound A used as the poorly water soluble substance in an Example below is crystalline and has crystalline polymorphs of type A (melting point: 119° C.) and type B (melting point: 161° C.). Provided that such a poorly water soluble substance exhibits crystalline polymorphism, the temperature of the composition just before flowing in the pulverization portion during operation of the high-pressure homogenizer must be determined with the melting point of the crystalline polymorph having the lowest melting point as the index.

Hence, when (i) poorly water soluble substance has crystalline polymorphs, and the melting point of the crystalline polymorph having the lowest melting point is not less than 140° C., it is preferable that the temperature of the composition just before flowing in the pulverization portion during operation of the high-pressure homogenizer be lower than the melting point of (i) poorly water soluble substance by not less than 100° C. By doing so, the elasticity of the poorly water soluble substance can sometimes be nullified, a feature suitable for pulverization.

When (i) poorly water soluble substance has crystalline polymorphs, and the melting point of the crystalline polymorph having the lowest melting point is less than 140° C., it is preferable that the temperature of the composition just before flowing in the pulverization portion during operation of the high-pressure homogenizer be not more than 40° C. By doing so, the elasticity of the poorly water soluble substance can sometimes be nullified, a feature suitable for pulverization.

In the present invention, whether or not the poorly water soluble substance has crystalline polymorph can be determined by attempting various methods of crystallization under various conditions, and analyzing the thus-obtained crystal by X-ray diffraction analysis, thermal analysis, density analysis, solubility analysis, microscopic observation and the like, and the melting point of the poorly water soluble substance, and, when poorly water soluble substance has crystalline polymorphs, the melting point of the crystalline polymorph having the lowest melting point are measured by using a thermal analyzer, for example, a differential scanning calorimeter (DSC).

The composition of the present invention is prepared by pulverizing (i) poorly water soluble substance and (ii) PVP or PVP-PVAc in a liquid, or by pulverizing (i) poorly water soluble substance, (ii) PVP or PVP-PVAc, and (iii) an auxiliary dispersion stabilizer in a liquid, as described above, and is used as is in the form of the thus-obtained pulverized suspension wherein the composition of the present invention is dispersed, or is used in the form of a powdery solid composition prepared by powdering the thus-obtained pulverized suspension by spray drying, freeze drying, vacuum drying and the like. Hence, when a powdery solid composition is to be obtained, after a step for pulverizing (i) poorly water soluble substance and (ii) PVP or PVP-PVAc in a liquid, or pulverizing (i) poorly water soluble substance, (ii) PVP or PVP-PVAc, and (iii) an auxiliary dispersion stabilizer in a liquid (step A), a step for powdering the pulverized suspension obtained in the step A (step B) is performed. By powdering the pulverized suspension, a powder comprising (i) a poorly water soluble substance and (ii) polyvinylpyrrolidone or a vinylpyrrolidone-vinyl acetate copolymer, or a powder comprising (i) a poorly water soluble substance, (ii) polyvinylpyrrolidone or a vinylpyrrolidone-vinyl acetate copolymer, and (iii) an auxiliary dispersion stabilizer is obtained, and the composition of the present invention is collected as a powder (solid composition). In powdering, if necessary, an anti-aggregation agent, an antistatic agent and the like can be added; as examples of the anti-aggregation agent, antisolidification agents such as talc, corn starch, hydrated silicone dioxide, Light Anhydrous Silicic Acid, and magnesium metasilicic aluminate, sugar alcohols such as lactose, mannitol (D-mannitol), and trehalose, and the like can be mentioned. As examples of the antistatic agent, talc, hydrated silicon dioxide, Light Anhydrous Silicic Acid and the like can be mentioned.

In addition to the above-described spray drying, freeze drying, vacuum drying and the like, the above-described powdering can also be achieved by a method comprising suspending and dispersing a liquid composition in a heat-melted wax etc. to be used as the liquid in step A, solidifying the liquid composition by returning the temperature to normal temperature, and pulverizing the solid product. The above-described powdering can also be achieved by a method comprising adding a heat-melted wax and the like to a pulverized suspension obtained via the step A, solidifying the mixture by returning the temperature to normal temperature, and pulverizing the solid product.

It is also possible to directly spraying the pulverized suspension obtained via the step A as a binder solution during spray drying, or during fluidized bed granulation, during tumbling fluidized granulation and during centrifugal tumbling granulation, to obtain a granulated powder. In this case, a binder can be newly added as required. The pulverized suspension can be added simply at the time of agitation granulation or extrusion granulation.

The composition of the present invention has a median diameter of not more than 1 μm. The term median diameter generally refers to the particle diameter corresponding to the median (frequency 50%) of the integral distribution curve generated from the particle size distribution indicating the number of particles per particle size class, and, in the present invention, refers to the particle diameter of 50% frequency as measured using a laser diffraction/scattering particle size distribution analyzer (LA-920, Horiba Ltd.) (50% frequency particle diameter). The dispersion medium used for the measurement is usually water, but an aqueous solution of a substance other than the poorly water soluble substance contained in the composition and the like (for some purposes, buffer solutions at various pH levels, mimicked body fluid, 0.5% methylcellulose aqueous solution and the like) can also be used. The suspending concentration of the composition at the time of measurement is measured after dilution with the dispersion medium used for the measurement so that the transmittance of the light source will be 80 to 99% compared to blank determinations.

The composition of the present invention preferably has a median diameter of not more than 0.8 μm, more preferably not more than 0.6 μm. Although the lower limit of the median diameter is not subject to limitation, the limit is generally preferably not less than 0.05 μm more preferably not less than 0.1 μm.

The composition of the present invention preferably has a 90% frequency particle diameter of not more than 2 μm, more preferably not more than 1 μm. "90% frequency particle diameter" is a particle diameter corresponding to the 90% frequency of the above-described integral distribution curve and, in the present invention, means the particle diameter of 90% frequency (90% frequency particle diameter) of the composition dispersed in a liquid, as measured using a laser diffraction/scattering particle size distribution analyzer (LA-920, Horiba Ltd.).

Because the composition of the present invention has the above-described particular particle size characteristics, the solubility of the poorly water soluble substance generally remains unchanged, the dissolution speed of the poorly water soluble substance is improved, and hence the absorption of the poorly water soluble substance is improved and variation in absorption is suppressed. In the composition of the present invention, degree of crystallinity as calculated from measurements taken using a powder X-ray diffraction apparatus remains almost unchanged compared to that before wet pulverization. However, depending on the properties of the poorly water soluble substance, the crystalline form sometimes changes after wet pulverization, and degree of crystallinity sometimes rises after wet pulverization.

Because the composition of the present invention has the above-described particular particle size characteristics, the dissolution rate of the poorly water soluble substance at 37° C. is accelerated not less than 2 times, preferably not less than 5 times, compared to conventional. The elution rate of the poorly water soluble substance is measured by the dissolution test method described below.

Dissolution Test Method
1) Test fluid: Sink conditions involving an S-index of not more than 2
2) Japanese Pharmacopoeia paddle method
3) Paddle rotation rate: 50 rpm
4) Test fluid temperature: 37° C.
5) Test fluid volume: 900 mL
6) Test environment: When the light stability of the poorly water soluble substance is low, the test is started in a shaded room, or in a room in the absence of light sources other than light sources deprived of particular wavelengths that influence the light stability, for example, in a room in the absence of light sources other than sodium lamps, after which 5 mL of test fluid is collected at specified time intervals using a syringe filter (manufactured by Nihon Pall Ltd., Acrodisc LC25, PVDF, pore diameter 0.2 um), the filtrate deprived of the first 3 mL is used as the sample solution. The concentration of the poorly water soluble substance in this sample solution is measured, and the dissolution rate is calculated. From the dissolution rate thus obtained, the dissolution speed is calculated by, for example, comparing times taken to reach a dissolution rate of not less than 85%.

The increase in the dissolution speed of the poorly water soluble substance in the present invention is attributable to an increase in surface area per unit weight of the poorly water soluble substance due to micronization, and, in the case of a water-repelling poorly water soluble substance, is also attributable to an improvement in wettability.

In the present invention, an improvement in the absorption of a poorly water soluble substance refers to an improvement in the absorption rate of the poorly water soluble substance or an improvement in the absorption amount of poorly water soluble substance; as indexes thereof, Cmax and AUC as mentioned in pharmacokinetics, respectively, can be mentioned. Cmax refers to the time to reach the maximum plasma concentration after administration; AUC refers to the area under the plasma concentration-time curve. Specifically, in the composition of the present invention, each of the Cmax and AUC of the poorly water soluble substance is improved not less than 2 times, preferably not less than 5 times, compared to conventional compositions.

The composition of the present invention is used as a drug, quasi-drug or food material in the form of the pulverized suspension after the aforementioned wet pulverization as is (that is, the suspension wherein the composition is dispersed in a liquid), or after being powdered from the pulverized suspension. Also, a powder obtained by powdering the pulverized suspension (solid composition) can be used as is, and can be used as a mixed powder prepared by adding a pharmaceutically acceptable appropriate excipient and the like. Although the powder or mixed powder thus obtained can be orally administered as is, it can be prepared as various forms of solid preparations commonly known as preparations for oral administration, that is, tablets, powders, granules, capsules and the like by a conventional method. The pulverized suspension can be used as is in the form of a liquid, and in the form of a capsular preparation filled in capsules, thus offering the advantage of reducing the number of steps for preparation making. By using a wax heat-melted in a liquid (dispersion medium) for pulverized suspensions, the composition of the present invention can also be prepared as a solid preparation integrally formed in a single process.

To obtain tablets or granules, the composition of the present invention can be prepared as film-coated tablets, film-coated granules and the like. The solid preparation can be given a sustained-release quality by conferring an appropriate release control function (prepared as a sustained release preparation). For example, the solid preparation is applicable to water soluble or wax matrix tablets, release control membrane coated granules or tablets, and dry coated tablets having a release control function.

The composition of the present invention is particularly suitable for assuring a long span of absorption required for sustained-release preparations. Hence, particularly, because a poorly water soluble substance is likely to lose the amount dissolved and have decreased absorption in the lower gastrointestinal tract, in which the water content is smaller than in the upper gastrointestinal tract, the composition of the present invention is effective in preparing the poorly water soluble substance as a sustained-release preparation.

When a solid preparation is obtained using the composition of the present invention, in addition to excipients, lubricants, binders, surfactants, disintegrants, coating agents and the like can be contained as required; when a liquid preparation is obtained, solvents, isotonizing agents, buffering agents, soothing agents and the like can be contained. Pharmaceutical preparation additives such as antiseptics, antioxidants, coloring agents, and taste correctives can also be contained as required.

The amount of poorly water soluble substance contained in the entire composition of the present invention differs depending on the intended use, dosage form, method of administration, and carrier of the poorly water soluble substance, and is generally preferably in the range from about 0.01 to about 99.99% (w/w), more preferably about 0.05 to about 99.9% (w/w). The amount of (ii) polyvinylpyrrolidone or a vinylpyrrolidone-vinyl acetate copolymer contained in the entire composition of the present invention is preferably about 0.01 to about 15% (w/w), more preferably about 0.05 to about 15% (w/w); the amount of (iii) auxiliary dispersion stabilizer contained is preferably about 0.01 to about 5% (w/w), more preferably about 0.05 to about 5% (w/w).

As examples of the excipient, lactose, starch, cornstarch, crystalline cellulose (manufactured by Asahi Kasei Corporation, Avicel PH101 (trade name) and the like), powdered sugar, granulated sugar, mannitol (D-mannitol), Light Anhydrous Silicic Acid, L-cysteine and the like can be mentioned. These excipients can be used singly or in combination of two or more kinds. The amount of excipient contained in the composition of the present invention is preferably about 0.1 to about 99.5% by weight, more preferably about 0.1 to about 99% by weight, particularly preferably about 0.1 to about 98% by weight.

As examples of the binder, sucrose, gelatin, acacia powder, methylcellulose, hydroxypropylcellulose, hydroxypropylmethylcellulose, carboxymethylcellulose, carboxymethylcellulose sodium, polyvinylpyrrolidone, vinylpyrrolidone-vinyl acetate copolymer, pullulan, dextrin and the like can be mentioned. These binders can be used singly or in combination of two or more kinds; the amount of binder contained in the composition of the present invention is preferably about 0.01 to about 30% by weight, more preferably about 0.03 to about 10% by weight. Even when such a binder is contained, the effect of this composition in the final preparation is not spoiled and good absorbability can be exhibited.

As examples of the disintegrant, crosslinked carmellose sodium (for example, Asahi Kasei Corporation, Ac-Di-Sol), crosslinked insoluble polyvinylpyrrolidone (for example, manufactured by BASF, Kollidon CL), low-substitutional hydroxypropylcellulose, partially gelatinized starch and the like), enteric polymers (for example, hydroxypropylmethylcellulose phthalate, cellulose acetate phthalate, carboxymethylcellulose and the like), water-insoluble polymers (for example, aminoalkyl methacrylate copolymer, methacrylic acid copolymer and the like) and the like can be mentioned; these disintegrants can be used singly or in combination of 2 or more kinds; the amount of disintegrant in the composition of the present invention is preferably about 0.1 to about 10% by weight, more preferably about 0.5 to about 7% by weight.

As examples of the surfactant, nonionic surfactants (for example, polyoxyethylene alkyl ethers, polyethylene glycol fatty acid esters, polyoxypropylene alkyl ethers, polypropylene glycol fatty acid esters, sorbitan fatty acid esters, polyoxyethylene sorbitan fatty acid esters, polyoxyethylene hardened castor oil, polyglycerin fatty acid esters, polyoxyethylene glycerin fatty acid esters, glycerin monofatty acid esters, alkyl polyglucoside, polyoxyethylene polyoxypropylene block polymers, alkanolamide and the like), ampholytic surfactants (alkyldimethylaminoacetic acid betaine, amidepropyldimethyl aminoacetic acid betaine, amide amino acid salts, alkylimino diacetic acid salts and the like), anionic surfactants (for example, alkyl sulfate ester salts, alkyl ether sulfate ester salts, α-olefin sulfonic acid salts, acylmethyl taurine salt, acylglutamic acid salts, acylglycine salts, acylsarcosine salts, acylisethionic acid salts, alkyl ether carboxylic acid salts, amide ether sulfate ester salts, alkyl phosphate ester salts and the like), cationic surfactants (for example, alkyltrimethylammonium chloride, dialkyldimethylammonium chloride and the like), bile acid and salts thereof, soaps and fatty acids, and salts thereof, oils, glycerin fatty acid esters, enamine, chelating agents, fatty acid derivatives such as phenothiazine, carnitine or peptides, a substance selected from the group consisting of azone, concanavalin A, diethyl maleate and diethylethoxymethylene malonate, Maillard reaction products, polymers (for example, block copolymers and biodegradable polymers, chitosan and chitosan derivatives) can be mentioned. Of these, surfactants, hydrophilic polymers, cyclodextrin derivatives, cholic acid derivatives and the like are preferable, and surfactants are particularly preferable. Of the surfactant, at least one selected from the group consisting of anionic surfactants, cationic surfactants and nonionic surfactants is preferable, particularly preferably an anionic surfactant; of the anionic surfactants, long-chain alkyl (preferably having a carbon number of 10 to 20) sulfates are preferable, most preferably sodium lauryl sulfate. The sodium lauryl sulfate mentioned herein is a single substance. In the present invention, surfactants can be used singly or in combination of two or more kinds. The surfactant content in the composition of the present invention is preferably about 0.01 to about 50% by weight, more preferably about 0.1 to about 30% by weight. Even when such a surfactant is contained, the effect of this composition in the final preparation is not spoiled and good absorbability can be exhibited.

As examples of the lubricant, magnesium stearate, sugar esters, talc and the like can be mentioned. As examples of the coloring agent, tar dyes, caramel, red iron oxide, titanium oxide, and riboflavins can be mentioned; as examples of the taste corrective, sweetening agents, flavoring agents and the like can be mentioned. As other additives that can be formulated in the composition of the present invention, adsorbents, antiseptics, wetting agents, antistatic agents, disintegration retarders and the like can be mentioned.

When the composition of the present invention is prepared in film-coated agents such as film-coated tablets and film-coated granules, plasticizers such as polyethylene glycol, dibutyl sebacate, diethyl phthalate, triacetin and triethyl citrate, stabilizers and the like can be used as required. The amount of coating substance is preferably about 0.01 to about 100% by weight, more preferably about 0.1 to about 80% by weight, and most preferably about 2 to about 50% by weight, relative to the core composition (the composition of the present invention).

Because the poorly water soluble substance in the composition of the present invention is micronized to exhibit good absorption, the use of the composition of the present invention makes it possible to realize a composition as effective as a conventional composition comprising the same poorly water soluble substance while reducing the amount of poorly water soluble substance contained in the composition compared to the conventional composition comprising the same poorly water soluble substance. Therefore, the composition of the present invention can also be prepared as a small, easily ingestible dosage form.

In the present invention, it is preferable that wet pulverization of a composition prepared by blending a poorly water soluble substance with polyvinylpyrrolidone or a vinylpyrrolidone-vinyl acetate copolymer be performed using a high-pressure homogenizer, but the aforementioned preferable content ratios in the composition of the present invention are of course applied to any other method of wet pulverization that the wet pulverization using a high-pressure homogenizer. This is because the pulverizer pulverizes a poorly water soluble substance into microparticles while providing energy, and the substance added as the dispersion stabilizer or both the substance added as the dispersion stabilizer and the substance added as the auxiliary dispersion stabilizer serve to suppress the aggregation of the poorly water soluble substance micronized in a liquid. Usually, if no appropriate dispersion stabilizer is added, the poorly water soluble substance pulverized by the pulverizer rapidly gets aggregated and is substantially unmicronizable.

In the present invention, the anti-aggregation performance of the poorly water soluble substance in liquid by content ratio of the composition can be evaluated by pulverization using a simple pulverizer (mechanical mixer), for example, ball mill and the like.

EXAMPLES

The present invention is explained in detail in the following by referring to Reference Examples, Comparative Examples and Examples, which are not to be construed as limitative.

Example 1

One kind of a substance (1 g) selected from the following group of poorly water soluble substances, Kollidon 17PF (0.15 g: manufactured by BASF Takeda vitamin (Co., Ltd.)), sodium lauryl sulfate (0.015 g), and purified water (5 g) were enclosed in a cylindrical stainless tube with an inner diameter of 17 mm and a length of 65 mm together with stainless balls (30 g) with a diameter of 1.6 mm. The tube was mounted on a Spex mixer/mill and shaken for 90 minutes to give a pulverized suspension. [poorly water soluble substance group]

Ketoprofen (analgesic antiphlogistic), nifedipine (hypotensors), indomethacin (analgesic antiphlogistic), glimepiride (antidiabetic drugs), griseofluvin (antifungal agent), sulfadimethoxine (antibacterial agent), 1-(4-{4-[(2-{(E)-2-[4-(trifluoromethyl) phenyl]ethenyl}-1,3-oxazol-4-yl) methoxy]phenyl}butyl)-1H-1,2,3-triazole (hereinafter to be referred to as "compound A")(anticancer agent).

Comparative Example 1

Sodium lauryl sulfate (2.4 g) was dissolved in purified water (400 g), Japanese Pharmacopoeia (JP) nifedipine (80 g: DAITO CO., Ltd.) was added thereto, and the mixture was stirred with a Three One Motor to allow dispersion. The dispersion was charged in a high-pressure homogenizer Microfluidizer M-110E/H (manufactured by Microfluidics), and pulverized at load pressure: 1500 bar, temperature of composition just before entry into a pulverizing part: 30° C., number of circulation of sample: 150 times, with a pulverization chamber Y and a Back Pressure-module mounted thereon, to give a pulverized suspension.

Comparative Example 2

In the same manner as in Comparative Example 1 except that the amount of sodium lauryl sulfate was set to 8.0 g, a pulverized suspension was obtained.

Comparative Example 3

In the same manner as in Comparative Example 1 except that sodium lauryl sulfate (2.4 g) was changed to polysorbate (3.0 g: manufactured by Wako Pure Chemical Industries, Ltd.), a pulverized suspension was obtained.

Comparative Example 4

In the same manner as in Comparative Example 1 except that sodium lauryl sulfate (2.4 g) was changed to Lutrol 68 (compound name: ABA block copolymer (polyoxyethylene (160)polyoxypropylene(30)glycol) of polyoxyethylene and polyoxypropylene, average polymerization degree: 30 for polyoxypropylene, 160 for polyoxyethylene) (16.0 g: manufactured by BASF Takeda Vitamin Co., Ltd.), a pulverized suspension was obtained.

Comparative Example 5

In the same manner as in Comparative Example 1 except that sodium lauryl sulfate (2.4 g) was changed to KollicoatIR (compound name: PEG-polyvinyl alcohol copolymer) (12.0 g: manufactured by BASF Takeda Vitamin Co., Ltd.) and sodium lauryl sulfate (1.2 g), a pulverized suspension was obtained.

Comparative Example 6

Kollidon 17PF (2.0 g: manufactured by BASF Takeda Vitamin Co., Ltd.) was dissolved in purified water (400 g), compound A (80 g) was added thereto, and the mixture was stirred by a Three One Motor to allow dispersion. The dispersion was charged in Microfluidizer M-110E/H (manufactured by Microfluidics), and pulverized at a load pressure: 1,500 bar, temperature of composition just before entry into a pulverizing part: 30° C., number of circulation of sample: 150 times, with a pulverization chamber Y and a Back Pressure module mounted thereon, to give a pulverized suspension.

Comparative Example 7

In the same manner as in Comparative Example 6 except that the amount of Kollidon 17PF was changed to 12.0 g, a pulverized suspension was obtained.

Example 2

In the same manner as in Comparative Example 1 except that sodium lauryl sulfate (2.4 g) was changed to Kollidon 17PF (2.0 g: manufactured by BASF Takeda Vitamin Co., Ltd.), a pulverized suspension was obtained.

Example 3

In the same manner as in Example 2 except that the amount of Kollidon 17PF was changed to 12.0 g, a pulverized suspension was obtained.

Example 4

In the same manner as in Example 2 except that Kollidon 17PF (2.0 g) was changed to Kollidon 17PF (2.0 g) and sodium lauryl sulfate (1.2 g), a pulverized suspension was obtained.

Example 5

In the same manner as in Example 4 except that the amount of Kollidon 17PF was changed to 4.0 g, a pulverized suspension was obtained.

Example 6

In the same manner as in Example 4 except that the amount of Kollidon 17PF was changed to 12.0 g, a pulverized suspension was obtained.

Example 7

In the same manner as in Example 5 except that compound A was added instead of Japanese Pharmacopoeia (JP) nifedipine, a pulverized suspension was obtained.

Example 8

In the same manner as in Example 6 except that compound A (80 g) was used instead of Japanese Pharmacopoeia (JP) nifedipine (80 g: manufactured by DAITO CO., Ltd.), a pulverized suspension was obtained.

Example 9

In the same manner as in Example 6 except that (+)-Griseofluvin (compound name: 7-chloro-2',4,6-trimethoxy-6'-methylspiro[benzofuran-2(3H),1'-[2]cyclohexene]-3,4'-dione) (80 g: manufactured by Acros chemicals) was used instead of Japanese Pharmacopoeia (JP) nifedipine (80 g: DAITO CO., Ltd.), a pulverized suspension was obtained.

Example 10

In the same manner as in Example 4 except that Kollidon 17PF (2.0 g) was changed to Kollidon 25 (2.0 g: manufactured by BASF Takeda Vitamin Co., Ltd.), a pulverized suspension was obtained.

Example 11

In the same manner as in Example 4 except that Kollidon 17PF (2.0 g) was changed to Kollidon 30 (12.0 g: manufactured by BASF Takeda Vitamin Co., Ltd.), a pulverized suspension was obtained.

Example 12

In the same manner as in Example 4 except that Kollidon 17PF (2.0 g) was changed to Kollidon 90F (0.08 g: manufactured by BASF Takeda Vitamin Co., Ltd.), a pulverized suspension was obtained.

Example 13

In the same manner as in Example 4 except that the amounts of Kollidon 17PF, sodium lauryl sulfate and Japanese Pharmacopoeia (JP) nifedipine were changed to 24.0 g, 2.4 g and 160 g, respectively, a pulverized suspension was obtained.

Example 14

In the same manner as in Example 4 except that a high-pressure homogenizer Microfluidizer M-210C (manufactured by Microfluidics) was used instead of Microfluidizer M-110E/H (manufactured by Microfluidics), a pulverized suspension was obtained.

Example 15

Kollidon 17PF (9.0 g) and sodium lauryl sulfate (0.9 g) were dissolved in purified water (300 g), Japanese Pharmacopoeia (JP) nifedipine (60 g: DAITO CO., Ltd.) was added and the mixture was stirred by a Three One Motor to allow dispersion. The dispersion was charged in a high-pressure homogenizer PA2K (manufactured by NiroSoavi), and pulverized at a load pressure: 1,500 bar, temperature of composition just before entry into a pulverizing part: 30° C., number of circulation of sample: 150 times to give a pulverized suspension.

Example 16

Kollidon 17PF (9.0 g) and sodium lauryl sulfate (0.9 g) were dissolved in purified water (300 g), Japanese Pharmacopoeia (JP) nifedipine (60 g: DAITO CO., Ltd.) was added and the mixture was stirred by a Three One Motor to allow dispersion. The dispersion was charged in a high-pressure homogenizer Ultimaizer HJP-25005 (manufactured by sugino machine), pulverized at a load pressure: 2,000 bar, temperature of composition just before entry into a pulverizing part: 30° C., number of circulation of sample: 350 times to give a pulverized suspension.

Example 17

Kollidon 17PF (120.0 g) and sodium lauryl sulfate (12.0 g) were dissolved in purified water (4000 g), Japanese Pharmacopoeia (JP) nifedipine (800 g: DAITO CO., Ltd.) was added thereto, and the mixture was stirred by a Three One Motor to allow dispersion. The dispersion was charged in a high-pressure homogenizer Ultimaizer (registered trademark) HJP-25080 (sugino machine), and pulverized at a load pressure: 2,000 bar, temperature of composition just before entry into a pulverizing part: 30° C., number of circulation of sample: 300 times to give a pulverized suspension.

Example 18

Kollidon 17PF (30.0 g) and sodium lauryl sulfate (3.0 g) were dissolved in purified water (1,000 g), Japanese Pharmacopoeia (JP) nifedipine (200 g: DAITO CO., Ltd.) was added thereto, and the mixture was stirred by a Three One Motor to allow dispersion. The dispersion was charged in a Microfluidizer M-110E/H (manufactured by Microfluidics), and pulverized at a load pressure: 1,500 bar, temperature of composition just before entry into a pulverizing part: 30° C., number of circulation of sample: 150 times, with a pulverization chamber Y and a Back Pressure module mounted thereon, to give a pulverized suspension.

Example 19

In the same manner as in Example 6 except that Copovidone VA64 was used instead of Kollidon 17PF, a pulverized suspension was obtained.

Example 20

In the same manner as in Comparative Example 1 except that the amounts of sodium lauryl sulfate, Kollidon 17PF, Japanese Pharmacopoeia (JP) nifedipine and purified water were changed to 3.0 g, 30 g, 200 g and 1000 g, respectively, a pulverized suspension was obtained. Then, D-mannitol (48 g) was added to the obtained pulverized suspension (616.5 g) and dissolved therein to give a suspension I.

D-mannitol (190 g) and crystalline cellulose (65.2 g, Avicel PH101, ASAHI KASEI CHEMICALS CORPORATION) were charged in a fluidized bed granulator (LAB-1, POWREX). The entire amount of the above-mentioned suspension I was sprayed thereon while flowing the mixture to give granules.

D-mannitol (2 g), croscarmellose sodium (2.24 g, Ac-Di-Sol, ASAHI KASEI CHEMICALS CORPORATION) and magnesium stearate (0.44 g, TAIHEI CHEMICAL INDUSTRIAL CO., LTD.) were added to and mixed with the obtained granules (41.97 g) to give a powder mixture.

The powder mixture was tabletted with a flat punch with a diameter of 10.5 mm under a tabletting pressure of 8 kN/tablet to give a plain tablet weighing 466.5 mg.

The plain tablet contains Japanese Pharmacopoeia (JP) nifedipine (100 mg), D-mannitol (258 mg), crystalline cellulose (65.2 mg), polyvinylpyrrolidone (15 mg), sodium lauryl sulfate (1.5 mg), croscarmellose sodium (22.4 mg) and magnesium stearate (4.4 mg) per tablet.

Example 21

In the same manner as in Example 20, a pulverized suspension was obtained.

D-mannitol (238 g) and crystalline cellulose (65.2 g, Avicel PH101, ASAHI KASEI CHEMICALS CORPORATION) were charged in a fluidized bed granulator (LAB-1, POWREX). The above-mentioned pulverized suspension (616.5 g) was sprayed thereon while flowing the mixture to give granules.

D-mannitol (2 g), croscarmellose sodium (2.24 g, Ac-Di-Sol, ASAHI KASEI CHEMICALS CORPORATION) and magnesium stearate (0.44 g, TAIHEI CHEMICAL INDUSTRIAL CO., LTD.) were added thereto and mixed with the obtained granules (41.97 g) to give a powder mixture.

The powder mixture was tabletted with a flat punch having a diameter of 10.5 mm under a tabletting pressure 8 kN/tablet to give a plain tablet weighing 466.5 mg.

The plain tablet contains Japanese Pharmacopoeia (JP) nifedipine (100 mg), D-mannitol (258 mg), crystalline cellulose (65.2 mg), polyvinylpyrrolidone (15 mg), sodium lauryl sulfate (1.5 mg), croscarmellose sodium (22.4 mg) and magnesium stearate (4.4 mg) per tablet.

Example 22

In the same manner as in Example 20, a pulverized suspension was obtained.

D-mannitol (238 g) and crystalline cellulose (65.2 g, Avicel PH101, ASAHI KASEI CHEMICALS CORPORATION) were charged in a fluidized bed granulator (LAB-1, POWREX). The above-mentioned pulverized suspension (616.5 g) was sprayed thereon while flowing the mixture to give granules.

D-mannitol (2 g), crospovidone (2.24 g, XL-10, YSP) and magnesium stearate (0.44 g, TAIHEI CHEMICAL INDUSTRIAL CO., LTD.) were added thereto and mixed with the obtained granules (41.97 g) to give a powder mixture.

The powder mixture was tabletted with a flat punch having a diameter of 10.5 mm under a tabletting pressure of 8 kN/tablet to give a plain tablet weighing 466.5 mg.

The plain tablet contains Japanese Pharmacopoeia (JP) nifedipine (100 mg), D-mannitol (258 mg), crystalline cellulose (65.2 mg), polyvinylpyrrolidone (15 mg), sodium lauryl sulfate (1.5 mg), crospovidone (22.4 mg) and magnesium stearate (4.4 mg) per tablet.

Example 23

In the same manner as in Example 20, a pulverized suspension was obtained.

D-mannitol (238 g) and crystalline cellulose (65.2 g, Avicel PH302, ASAHI KASEI CHEMICALS CORPORATION) were charged in a fluidized bed granulator (LAB-1, manufactured by POWREX CORPORATION). The above-mentioned pulverized suspension (616.5 g) was sprayed thereon while flowing the mixture to give granules.

D-mannitol (2 g), crospovidone (2.24 g, XL-10, YSP) and magnesium stearate (0.44 g, TAIHEI CHEMICAL INDUSTRIAL CO., LTD.) were added thereto and mixed with the obtained granulates (41.97 g) to give a powder mixture.

The powder mixture was tabletted with a flat punch having a diameter of 10.5 mm under a tabletting pressure of 8 kN/tablet to give a plain tablet weighing 466.5 mg.

The plain tablet contains Japanese Pharmacopoeia (JP) nifedipine (100 mg), D-mannitol (258 mg), crystalline cellulose (65.2 mg), polyvinylpyrrolidone (15 mg), sodium lauryl sulfate (1.5 mg), crospovidone (22.4 mg) and magnesium stearate (4.4 mg) per tablet.

Example 24

In the same manner as in Example 20, a pulverized suspension was obtained.

D-mannitol (238 g) and crystalline cellulose (65.2 g, Avicel PH302, ASAHI KASEI CHEMICALS CORPORATION) were charged in a fluidized bed granulator (LAB-1, POWREX). The above-mentioned pulverized suspension (616.5 g) was sprayed thereon while flowing the mixture to give granules.

D-mannitol (1 g), croscarmellose sodium (3.24 g, Ac-Di-Sol, ASAHI KASEI CHEMICALS CORPORATION) and magnesium stearate (0.44 g, TAIHEI CHEMICAL INDUSTRIAL CO., LTD.) were added to and mixed with the obtained granules (41.97 g) to give a powder mixture.

The powder mixture was tabletted with a flat punch having a diameter of 10.5 mm under a tabletting pressure of 8 kN/tablet to give a plain tablet weighing 466.5 mg.

The plain tablet contains Japanese Pharmacopoeia (JP) nifedipine (100 mg), D-mannitol (248 mg), crystalline cellulose (65.2 mg), polyvinylpyrrolidone (15 mg), sodium lauryl sulfate (1.5 mg), croscarmellose sodium (32.4 mg) and magnesium stearate (4.4 mg) per tablet.

Reference Example 1

A pulverization intermediate step product was obtained by collecting about 50 ml of the sample at the time point of number of circulation of sample: 5 times in Example 17.

Reference Example 2

A pulverized product of Japanese Pharmacopoeia (JP) nifedipine was used as it was.

Reference Example 3

A pulverized product of Japanese Pharmacopoeia (JP) nifedipine and D-mannitol were thoroughly mixed in a mortar at a weight ratio of 1:4 to give a powder mixture.

Experimental Example 1-1

Degree of Crystallinity of Composition After Pulverization

A powder obtained by freeze-drying the pulverized suspension obtained in Example 1 was enclosed in a quartz glass capillary and measured using a powder X-ray diffraction measurement apparatus (Rigaku Corporation, ultraX TTR2-300), Cu rotating target, parallel beam method (50 kV, 300 mA), scanning angle 3-120 degrees, scan step 0.02 degree/counting time 0.6 sec. The degree of crystallinity was calculated from the obtained X-ray diffraction profile using the Vonk method. The results are shown in the following Table 1. As a representative example, the results of an example using nifedipine, compound A, indomethacin and glimepiride as poorly water soluble substances are shown.

Figure 2:
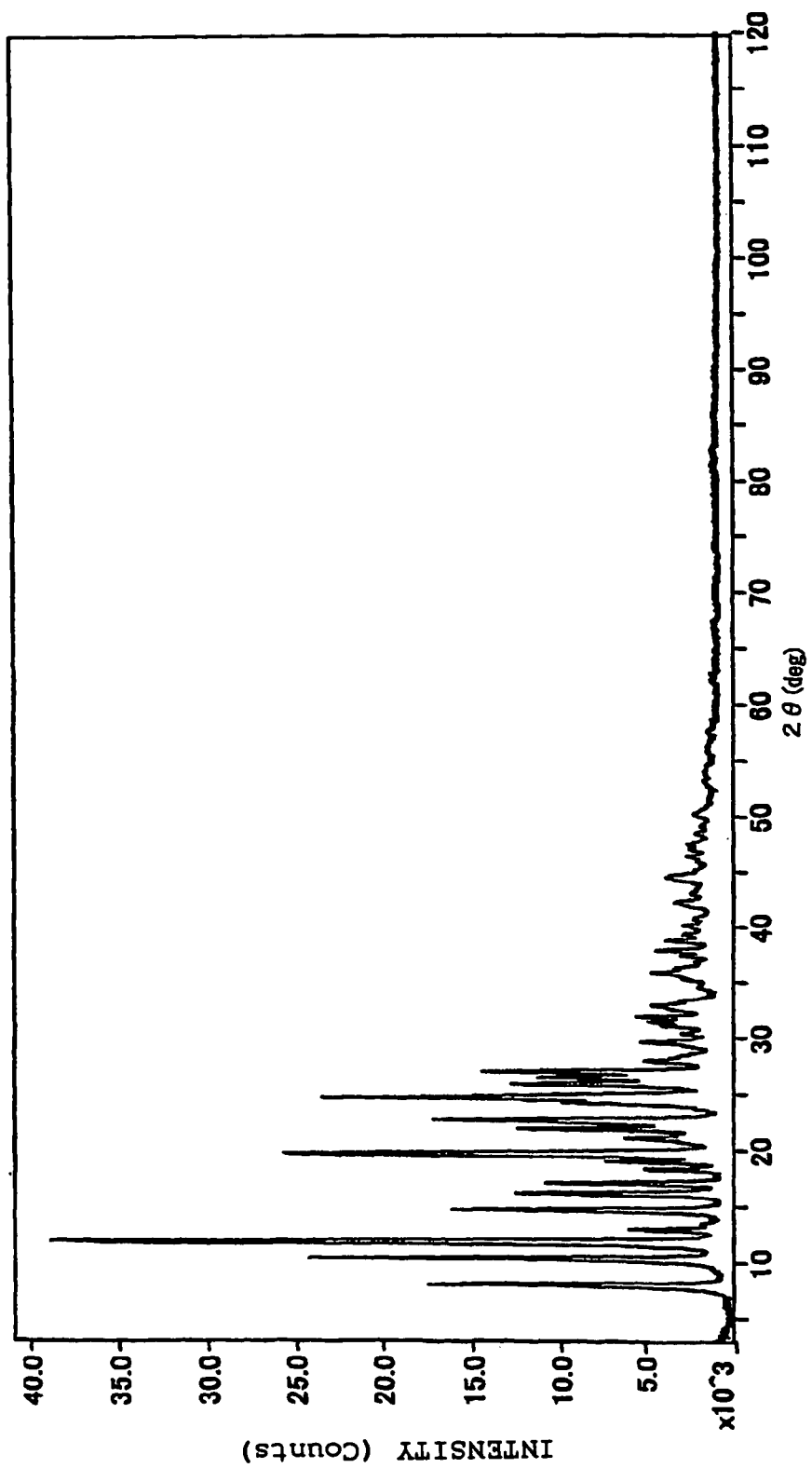
FIG. 2 is a powder X-ray diffraction chart of nifedipine (after pulverization).

FIGS. 1 and 2 are X-ray diffraction profiles of nifedipine before and after pulverization. It is appreciated from FIGS. 1 and 2 that nifedipine is crystal and maintains an almost crystal state. The X-ray diffraction profiles were obtained by measurements using the above-mentioned measurement apparatuses and conditions.

TABLE 1

| substance | before pulverization | | after pulverization | |
| --- | --- | --- | --- | --- |
| | degree of crystallinity (%) | turbulent factor | degree of crystallinity (%) | turbulent factor |
| nifedipine | 83.3 | 0.364 | 70.5 | 1.154 |
| compound A | 74.7 | −0.163 | 61.3 | 1.412 |
| indomethacin | 99.9 | −0.001 | 89.8 | 0.793 |
| glimepiride | 73.7 | 0.622 | 68.7 | 2.249 |

From Table 1, it is appreciated that the degree of crystallinity of each substance decreased somewhat after pulverization, but the turbulent factor increased simultaneously. The turbulent factor indicates that the molecules move about during X-ray measurement and that the diffraction intensity decreases. Considering that the below-mentioned solubility and fusion enthalpy are almost unchanged before and after pulverization, the above-mentioned certain decrease in the degree of crystallinity is considered to be attributable to a decrease in the diffraction intensity due to micronization, and the actual degree of crystallinity is considered to have hardly changed.

Experimental Example 1-2-1

Solubility of Composition after Pulverization

The pulverized suspension obtained in Example 1 was ultracentrifuged using a compact ultracentrifugation machine (manufactured by Hitachi, Ltd., CS120FX, rotor: S100AT5 angle rotor) at 100,000 rpm/min and 20° C. for 30 min. The supernatant at the central portion was gently collected in an injection syringe with a 26 gauge injection needle and the concentration thereof was measured using high performance liquid chromatography (HPLC) under the following conditions. The results thereof are shown in the following Table 2. As a representative example, the results of an example wherein nifedipine was used as a poorly water soluble substance are shown in Table 2-1 together with the concentration of poorly water soluble substance before pulverization.
(Measurement Conditions)
1) column trade name: Intersil ODS-3 (manufactured by GL Sciences Inc.)
 filler particle size: 5 μm
 column size: 4.6 mmφ×150 mm
2) eluent: 10 mM $CH_3COONH_4$/MeCN=6/4 (v/v)
3) wavelength: UV 325 nm
4) flow rate: 1 ml/min
5) injection cycle: 14 min
6) injection volume: 10 μl

TABLE 2-1

| Substance | before pulverization | after pulverization |
| --- | --- | --- |
| | solubility (μg/ml) | |
| nifedipine | 263.8 | 294.7 |

Experimental Example 1-2-2

Dissolution Rate of Composition After Pulverization

The pulverized suspension obtained in Example 1 and the powder mixture obtained in Reference Example 3 (each in an amount corresponding to 100 mg as nifedipine) were fed and a dissolution test was carried out under the following conditions.
1) test solution: phosphate buffer (50 mM, pH 6.8) containing dodecylsodium sulfate (0.5% (v/w))
2) Japanese Pharmacopoeia (JP) Paddle Method
3) paddle rotation speed: 50 rpm/min
4) temperature of test solution: 37° C.
5) amount of test solution: 900 mL
6) test environment: room excluding light sources other than a sodium lump After the start of the test, a test solution (5 mL) was collected at every predetermined time and a filtrate excluding the initial 3 mL was obtained as a sample solution using a syringe filter (manufactured by Pall Corporation, AcroDisk LC25, PVDF, pore size 0.2 um). The sample solution was diluted 2-fold with the eluent of Experimental Example 1-2-1 and the concentration of nifedipine in the sample solution was determined under the measurement conditions of Experimental Example 1-2-1, based on which the dissolution ratio was calculated. The results thereof are shown in Table 2-2.

TABLE 2-2

| | dissolution rate (%) | | | | |
| --- | --- | --- | --- | --- | --- |
| | 5 min | 10 min | 15 min | 30 min | 45 min |
| Example 1 | 101.5 | 98.5 | 100.9 | 100.6 | 100.0 |
| Reference Example 3 | 59.6 | 69.0 | 76.4 | 83.1 | 88.5 |

Experimental Example 1-3

Fusion Enthalpy of Composition after Pulverization

The powder obtained by freeze-drying the pulverized suspension obtained in Example 1 was measured using a differential calorimeter (DSC) at a scanning temperature of 0° C.-350° C. and a rate of temperature rise of 10° C./min, and fusion enthalpy were calculated by correcting the melting peak using a sample weight. The results thereof are shown in the following Table 3. As a representative example, the results of an example wherein nifedipine was used as a poorly water soluble substance are shown together with the fusion enthalpy of the poorly water soluble substance before pulverization.

TABLE 3

| substance | before pulverization | after pulverization |
| --- | --- | --- |
| | fusion enthalpy (J/g) | |
| nifedipine | −67.6 | −67.7 |

Experimental Example 1-4

Melting Point

The melting points of the poorly water soluble substances used in Example 1 were measured using a differential calorimeter (DSC) at a scanning temperature of 0° C.-350° C. and a rate of temperature rise of 10° C./min.

Experimental Example 2-1

Particle Size Measurement

The particle size of the pulverized suspensions obtained in Reference Examples 1-2, Comparative Examples 1-7, and Examples 1, 2-19 was measured using a laser diffraction/scattering particle size distribution analyzer LA-920 (Horiba, Ltd.). As a dispersion medium, purified water was used.

In the following Table 4, the melting points of the respective poorly water soluble substances used in Example 1, which were measured in the above-mentioned Experimental Example 1-4, as well as the median size (D50) before pulverization, median size (D50) after pulverization and 90% frequency particle size (D90) after pulverization of the respective poorly water soluble substances used in Example 1, which were measured in the above-mentioned Experimental Example 2-1 are shown. The following Table 5-1 shows the particle sizes (median size (D50), 90% frequency particle size (D90)) of the pulverized suspensions obtained in Reference Example 1-2, Comparative Example 1-7, and Example 2-19.

TABLE 4

| substance | melting point (°C.) | before pulverization particle size: D50 (μm) | after pulverization particle size: D50 (μm) | D90 (μm) |
|---|---|---|---|---|
| ketoprofen | 94-97 | — | 0.50 | 0.77 |
| nifedipine | 171-175 | 11.15 | 0.59 | 0.95 |
| Compound A | 119, 161 | 5.68 | 0.42 | 0.68 |
| indomethacin | 155, 162 | 9.61 | 0.36 | 0.50 |
| glimepiride | 205-208 | 1.67 | 0.39 | 0.55 |
| griseofluvin | 220 | 6.35 | 0.35 | 0.50 |
| sulfadimethoxine | 201-203 | — | 0.44 | 0.65 |

TABLE 5-1

| | D50 (μm) | D90 (μm) |
|---|---|---|
| Reference Example 1 | 2.25 | 3.91 |
| Reference Example 2 | 17.8 | 29.91 |
| Comparative Example 1 | 0.80 | 1.51 |
| Comparative Example 2 | 0.87 | 1.67 |
| Comparative Example 3 | 1.04 | 2.60 |
| Comparative Example 4 | 0.85 | 1.51 |
| Comparative Example 5 | 0.96 | 1.51 |
| Comparative Example 6 | pulverization unavailable due to creaming | |
| Comparative Example 7 | pulverization unavailable due to creaming | |
| Example 2 | 0.49 | 0.77 |
| Example 3 | 0.44 | 0.67 |
| Example 4 | 0.47 | 0.77 |
| Example 5 | 0.55 | 0.88 |
| Example 6 | 0.51 | 0.77 |
| Example 7 | 0.42 | 0.67 |
| Example 8 | 0.40 | 0.77 |
| Example 9 | 0.58 | 0.99 |
| Example 10 | 0.49 | 0.77 |
| Example 11 | 0.57 | 0.77 |
| Example 12 | 0.61 | 0.88 |
| Example 13 | 0.58 | 0.88 |

TABLE 5-1-continued

| | D50 (μm) | D90 (μm) |
|---|---|---|
| Example 14 | 0.41 | 0.58 |
| Example 15 | 0.80 | 1.15 |
| Example 16 | 0.49 | 0.77 |
| Example 17 | 0.44 | 0.67 |
| Example 18 | 0.48 | 0.67 |
| Example 19 | 0.57 | 0.88 |

Experimental Example 2-2

Measurement of Particle Size of Powder

The pulverized suspension (5 mL) taken in the intermediate step of Example 7 was placed in a 20 mL glass vial, and freeze-dried at −30° C. The obtained powder was directly fed in a laser diffraction/scattering particle size distribution analyzer LA-920 (Horiba, Ltd.) and the particle size was measured. As the dispersion medium, purified water was used. The obtained particle size and the particle size of the pulverized suspension before freeze-drying were compared and are shown in Table 5-2.

TABLE 5-2

| Example 7 intermediate step product | D50 (μm) | D90 (μm) |
|---|---|---|
| suspension | 0.71 | 1.15 |
| powder | 0.76 | 1.15 |

Experimental Example 3

Absorption Evaluation

The pulverized suspensions obtained in Reference Examples 1, 2 and Example 17 in a dose of 100 mg as nifedipine were administered p.o. to 6 male beagle dogs under fasting. After 30 min, 1, 2, 3, 4, 6, 8, 10, 12 and 24 hr from the administration, the blood was sampled from the Cephalic vein of the forefoot using an injection syringe equipped with a heparin-treated 23 gauge injection needle. After centrifugal fractionation, nifedipine concentration in the plasma component was measured by high performance liquid chromatography (HPLC). The area under the plasma concentration curve (AUC) was calculated by the trapezoid method and used as an index of absorption amount. In addition, dispersion in the areas under the plasma concentration curve (AUC) of individual dogs was calculated as a coefficient of variation (C.V. value). The results are shown in the following Table 6.

TABLE 6

| Samples | dose (mg/dog) | AUC 0-24 h (μg · h/mL) | C.V. (%) |
|---|---|---|---|
| Example 17 | 100 | 1.530 | 38.1 |
| Reference Example 1 | | 1.057 | 39.5 |
| Reference Example 2 | | 0.618 | 75.2 |

From Table 6, it is appreciated that micronized Example 17 and micronized intermediate step product of Reference Example 1 showed increased areas under the plasma concentration curve (AUC) as compared to Reference Example 2 before pulverization and improved absorption. In addition, C.V. value decreased from 75% to 38-39%, thus suppressing dispersed absorption.

Experimental Example 4

Tablet Property Evaluation

The plain tablet obtained in Example 20 was subjected to the disintegration test described in the Japan Pharmacopoeia fourteenth revision using a disintegration tester (NT-20H, Toyama Sangyo Co., Ltd.). In addition, the destruction hardness was measured using a tablet hardness tester (TH-303MP, Toyama Sangyo Co., Ltd.). The results are shown in the following Table 7.

TABLE 7

| sample | Example 20 |
|---|---|
| hardness (N, min.-max.) | 115-122 |
| disintegration time (min) | 4.00 |

From the results of the above-mentioned Examples 1-19, Comparative Examples 1-7 and Reference Examples 1, 2, it is appreciated that, according to the present invention, a poorly water soluble substance is sufficiently micronized to acquire sufficiently improved absorbability while maintaining a crystal state where a poorly water soluble substance is considered to be chemically and physically stable, and a micronized composition containing the poorly water soluble substance can be obtained. In particular, the absorption amount of a poorly water soluble substance can be increased, the dispersion in the absorption amount can also be suppressed, and a poorly water soluble substance can be stably absorbed.

From the results of the above-mentioned Examples 20-24, it is appreciated moreover that the composition of the present invention can be processed into a superior preparation by conventional steps without adding a special step.

INDUSTRIAL APPLICABILITY

As is clear from the foregoing explanation, according to the present invention, a poorly water soluble substance is sufficiently micronized and a composition containing a poorly water soluble substance showing good absorbability of the poorly water soluble substance can be provided. In addition, a production method of a composition containing a poorly water soluble substance capable of producing the composition efficiently is provided.

The composition containing a poorly water soluble substance of the present invention can also be obtained as a powder (solid), which can be used as it is (use in a powder state), or prepared into a solid dosage form for oral administration in various forms such as tablet, powder, granule, capsule and the like according to a conventional method. Moreover, a suspension of the composition containing a poorly water soluble substance of the present invention can be directly used as a liquid. Therefore, according to the composition of the present invention, for example, pharmaceutical preparations in various dosage forms showing good absorbability of a drug, which is a poorly water soluble substance, can be realized.

This application is based on a patent application No. 2005-022124 filed in Japan, the contents of which are incorporated in full herein by this reference.

The invention claimed is:

1. A method of producing a composition having a median diameter of not more than 1 μm, and comprising (i) a poorly water soluble substance, (ii) polyvinylpyrrolidone or vinylpyrrolidone-vinyl acetate copolymer and (iii) an auxiliary dispersion stabilizer, the method comprising: pulverizing (i) a poorly water soluble substance, (ii) polyvinylpyrrolidone or vinylpyrrolidone-vinyl acetate copolymer and (iii) an auxiliary dispersion stabilizer in a liquid using a high pressure homogenizer,
    wherein when the poorly water soluble substance has a melting point of not less than 140° C., the temperature of the composition just before flowing in the pulverization portion during operation of the high-pressure homogenizer is lower by not less than 100° C. than the melting point of the poorly water soluble substance, and
    wherein when the poorly water soluble substance has a melting point of less than 140° C., the temperature of the composition just before flowing in the pulverization portion during operation of the high-pressure homogenizer is not more than 40° C.

2. The method of claim 1, wherein the auxiliary dispersion stabilizer is at least one selected from the group consisting of a surfactant, a hydrophilic polymer, a cyclodextrin derivative and a cholic acid derivative.

3. The method of claim 2, wherein the surfactant is at least one selected from the group consisting of an anionic surfactant, a cationic surfactant and a nonionic surfactant.

4. The method of claim 1, wherein the auxiliary dispersion stabilizer is a long-chain alkyl sulfate salt.

5. The method of claim 4, wherein the long-chain alkyl sulfate salt is sodium lauryl sulfate.

6. The method of claim 4, wherein the solubility of the poorly water soluble substance in water is less than 1 μg/ml at 37° C.

7. The method of claim 1, wherein the content ratio by weight of (i) the poorly water soluble substance, (ii) the polyvinylpyrrolidone or vinylpyrrolidone-vinyl acetate copolymer, and (iii) the auxiliary dispersion stabilizer is 99.98 to 80.0:0.01 to 15.0:0.01 to 5.0.

8. The method of claim 1, wherein the pressure exerted on the high-pressure homogenizer is not less than 500 bar and not more than 5000 bar.

9. The method of claim 1, wherein provided that (i) the poorly water soluble substance has crystalline polymorphs, and the melting point of the crystalline polymorph having the lowest melting point is not less than 140° C., the temperature of the composition just before flowing in the pulverization portion during operation of the high-pressure homogenizer is lower by not less than 100° C. than the melting point of (i) the poorly water soluble substance.

10. The method of claim 1, wherein provided that (i) the poorly water soluble substance has crystalline polymorphs, and the melting point of the crystalline polymorph having the lowest melting point is less than 140° C., the temperature of the composition just before flowing in the pulverization portion during operation of the high-pressure homogenizer is not more than 40° C.

11. The method of claim 1, wherein the composition has a 90% frequency particle diameter of not more than 2 μm.

12. The method of claim 1, wherein (i) the poorly water soluble substance occurs as crystalline microparticles.

13. The method of claim 1, wherein the solubility of the poorly water soluble substance in water is not less than 1 μg/ml at 37° C. and not more than 0.1 mg/ml at 37° C.

14. The method of claim 1, wherein the solid concentration of (i) the poorly water soluble substance in a liquid is 10 to 60% by weight.

15. The method of claim 1, wherein the liquid is water.

16. A method of producing a composition having a median diameter of not more than 1 μm, and comprising (i) a poorly water soluble substance, (ii) polyvinylpyrrolidone or vinylpyrrolidone-vinyl acetate copolymer and (iii) an auxiliary dispersion stabilizer, the method comprising: pulverizing (i) a poorly water soluble substance, (ii) polyvinylpyrrolidone or vinylpyrrolidone-vinyl acetate copolymer and (iii) an auxiliary dispersion stabilizer in a liquid using a high pressure homogenizer, wherein when the poorly water soluble substance has crystalline polymorphs, and the melting point of the crystalline polymorph having the lowest melting point is not less than 140° C., the temperature of the composition just before flowing in the pulverization portion during operation of the high-pressure homogenizer is lower by not less than 100° C. than the melting point of the poorly water soluble substance, and wherein when the poorly water soluble substance has crystalline polymorphs, and the melting point of the crystalline polymorph having the lowest melting point is less than 140° C., the temperature of the composition just before flowing in the pulverization portion during operation of the high-pressure homogenizer is not more than 40° C.

17. The method of claim 16, wherein the auxiliary dispersion stabilizer is at least one selected from the group consisting of a surfactant, a hydrophilic polymer, a cyclodextrin derivative and a cholic acid derivative.

18. The method of claim 17, wherein the surfactant is at least one selected from the group consisting of an anionic surfactant, a cationic surfactant and a nonionic surfactant.

19. The method of claim 16, wherein the auxiliary dispersion stabilizer is a long-chain alkyl sulfate salt.

20. The method of claim 19, wherein the long-chain alkyl sulfate salt is sodium lauryl sulfate.

21. The method of claim 19, wherein the solubility of the poorly water soluble substance in water is less than 1 μg/ml at 37° C.

22. The method of claim 16, wherein the content ratio by weight of (i) the poorly water soluble substance, (ii) the polyvinylpyrrolidone or vinylpyrrolidone-vinyl acetate copolymer, and (iii) the auxiliary dispersion stabilizer is 99.98 to 80.0:0.01 to 15.0:0.01 to 5.0.

23. The method of claim 16, wherein the pressure exerted on the high-pressure homogenizer is not less than 500 bar and not more than 5000 bar.

24. The method of claim 16, wherein the composition has a 90% frequency particle diameter of not more than 2 μm.

25. The method of claim 16, wherein the poorly water soluble substance occurs as crystalline microparticles.

26. The method of claim 16, wherein the solubility of the poorly water soluble substance in water is not less than 1 μg/ml at 37° C. and not more than 0.1 mg/ml at 37° C.

27. The method of claim 16, wherein the solid concentration of the poorly water soluble substance in a liquid is 10 to 60% by weight.

28. The method of claim 16, wherein the liquid is water.

* * * * *

UNITED STATES PATENT AND TRADEMARK OFFICE
CERTIFICATE OF CORRECTION

PATENT NO.       : 8,623,405 B2  
APPLICATION NO. : 11/795734  
DATED            : January 7, 2014  
INVENTOR(S)      : Suzuki et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1258 days.

Signed and Sealed this
Twenty-second Day of September, 2015

Michelle K. Lee
*Director of the United States Patent and Trademark Office*